(12) United States Patent
Goodship et al.

(10) Patent No.: US 6,255,288 B1
(45) Date of Patent: Jul. 3, 2001

(54) CERTAIN METHANEBISPHOSPHONIC ACID DERIVATIVES IN FRACTURE HEALING

(75) Inventors: Allen E. Goodship; Peter Walker, both of Bristol; Donal S. McNally, Bradley Stoke North; Timothy J. Chambers, London, all of (GB); Jonathan Green, Arlesheim (CH)

(73) Assignee: Novartis Corporation, New York, NY (US)

( * ) Notice: Subject to any disclaimer, the term of this patent is extended or adjusted under 35 U.S.C. 154(b) by 0 days.

(21) Appl. No.: 08/159,096

(22) Filed: Nov. 29, 1993

(30) Foreign Application Priority Data

Nov. 30, 1992 (EP) .................................................. 92810931

(51) Int. Cl.$^7$ ............................... A01N 43/04; C07F 9/22
(52) U.S. Cl. ................................................. 514/41; 562/13
(58) Field of Search ............................... 562/13; 514/410

(56) References Cited

U.S. PATENT DOCUMENTS

| | | |
|---|---|---|
| 4,687,767 | 8/1987 | Bosies et al. . |
| 4,857,513 | 8/1989 | Oku et al. . |
| 4,927,814 | 5/1990 | Gall et al. . |
| 4,942,157 | 7/1990 | Gall et al. . |
| 4,963,536 | 10/1990 | Oku et al. . |
| 5,057,505 | 10/1991 | Widler et al. . |

FOREIGN PATENT DOCUMENTS

| | | |
|---|---|---|
| 0252505 | 1/1988 | (EP) . |
| 205061 | 8/1987 | (NZ) . |
| 222610 | 9/1990 | (NZ) . |
| 234377 | 8/1992 | (NZ) . |
| 234378 | 8/1992 | (NZ) . |
| 9221355 | 12/1992 | (WO) . |

OTHER PUBLICATIONS

Kanis, Treatment of Osteoporotic Fracture, Lancet 1984, p. 27–33 (1984).
Reid et al, Prevention of Steroid–Induced Osteoporosis with (3–Amino–1–Hydroxypropylidene)–1,1–Bisphosphonate (APD), Lancet 1988, p. 143–146 (1988).
Alpar, Questions and Answers Can Drugs Influence the Bone Healing Process, J. Clin. Hosp. Pharmacy 9, p. 341–344 (1984).

Finerman et al, Diphosphonate Treatment of Paget's Disease, Clin. Orthopaed. Rel. Res. 120, p. 115–124 (1976).

Flora et al, The Long Term Skeletal Effects of EHDP in Dogs, Metab. Bone Dis. Rel. Res. 4/5, p. 289–300 (1981).

Lenehan et al, Effect of EHDP on Fracture Healing in Dogs, J. Orthopaedic Res. 3, p. 499–507 (1985).

Stumpf, Pharmacologic Management of Paget's Disease, Clinical Pharmacy 8, p. 485–495 (1989).

Fitton et al, Pamidronate A Review of its Pharmacological Properties and Therapeutic Efficacy in Resorptive Bone Disease, Drugs 41, p. 289–318 (1991).

Henricson et al, The Effect of Diphosphonates on Fracture healing in Rats Studied With Monoclonal Antibodies, Calcified Tissue Int. 39(Suppl), A74 (1986).

Goodship et al, The Modulation of the Morphology and Mechanical Properties of Fracture Repair During Bisphosphonate (Pamidronate) Treatment, 39$^{th}$ Annual Meeting, Orthopaedic Research Society, Feb. 15–18, 1993, San Francisco, CA.

*Primary Examiner*—C. H. Kelly
(74) *Attorney, Agent, or Firm*—Carol A. Loeschron

(57) ABSTRACT

The invention relates to the use of methanebisphosphonic acid derivatives of formula I

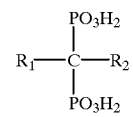

for the treatment of fractures. These compounds have surprisingly been found to promote a more rapid and stronger fracture healing in mammals including man.

14 Claims, No Drawings

CERTAIN METHANEBISPHOSPHONIC ACID DERIVATIVES IN FRACTURE HEALING

Methanebisphosphonic acid derivatives, in particular bisphosphonate compounds, are used clinically to inhibit excessive bone resorption in a variety of diseases such as tumour-induced osteolysis, Paget's disease and osteoporosis. Radiolabelled bisphosphonates are also used diagnostically to identify sites of high bone turnover.

As the compounds bind to bone mineral and inhibit bone resorption, there has been general concern that bisphosphonates could have a deleterious effect on callus formation and remodelling, which is an essential part of the fracture repair process. Kanis, for example, teaches in Lancet 1984, 27–33 that bisphosphonates, as inhibitors of bone resorption, may indeed halt skeletal losses but on the other hand delay the repair of microfractures by reducing the rate of remodelling of damaged bone and inhibiting callus formation. As another example, Reid et al. in Lancet 1988, 143–146 found that bisphosphonate treatment, in this particular case done with disodium pamidronate (=APD), caused a reduction in bone formation and a very low rate of bone turnover which raised the possibility of impaired microfracture repair. Furthermore, Alpar, in J. Clin. Hosp. Pharmacy 9 (1984) 341–344, expressed the view that the natural process of bone healing cannot be influenced by any drug.

Furthermore, one commercially available bisphosphonate, disodiumn etidronate, is even known to inhibit bone mineralization and to delay callus formation and fracture healing in man and animals at doses within the therapeutic range [see G. A. M. Finelllan et al., Clin. Orthopaed. Rol. Res. 120 (1976) 115–124; L. Flora et al., Metabol. Bone Dis. Rel. Res. 4/5 (1981) 289–300].

Very surprisingly, it has now been found that certain methanebisphosphonic acid derivatives have a highly beneficial effect on fracture repair. In vivo experiments show that in the treated animals, e.g. sheep, there is a more prolific callus and the ultimate torsional strength of the healing osteotomy is significantly greater, whereas fracture stiffness remains unaffected. These results show that it is possible to use said methanebisphosphonic acid derivatives to promote a more rapid and stronger fracture healing.

The invention therefore relates to the use of a methanebisphosphonic acid derivative of formula I

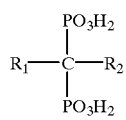

(I)

wherein
(a) $R_1$ and $R_2$ are each independently of the other halogen or
(b) $R_1$ is hydrogen and $R_2$ is a group Ar—S—, $Het_1$—NH—, Cyc—NH—, Ar—S—A—N(R')—, $Het_3$—S—A—N(R')— or is N-phenylthiocarbamoyl, wherein Ar is unsubstituted or substituted phenyl, $Het_1$ and $Het_3$ are each unsubstituted or substituted monocyclic 5- or 6-membered monoaza-, diaza- or thiaza-aryl which is bound through a ring carbon atom, Cyc is cycloalkyl, A is alkylene and R' is hydrogen or lower alkyl, or
(c) $R_1$ is hydrogen or hydroxy and $R_2$ is —A—$R_3$, wherein A is alkylene, and
$R_3$ is either Ar as defined above or is $Het_2$, which has the meaning of $Het_1$ but can be bound through a ring carbon atom or a ring nitrogen atom, or $R_3$ is unsubstituted or substituted bicyclic monoaza-, diaza- or triaza-aryl which is bound through a ring carbon atom or a ring nitrogen atom, or
$R_3$ is unsubstituted amino or amino which is mono- or disubstituted by alkyl, cycloalkyl, Ar-alkyl, Ar—O-alkyl, Ar—S-alkyl or $Het_1$-alkyl each independently of one another, and Ar and $Het_1$ are as defined above, or
$R_3$ is unsubstituted or Ar-substituted alkyleneamino, wherein two alkylene carbon atoms may be additionally linked to each other through alkylene, and Ar is as defined above,
or of the methanebisphosphonic acid esters 5-benzoyl-3,4-dihydro-2H-pyrazole-3,3-diphosphonic acid tetraethyl ester or 1-(4-phenylthiobutylamino)methane-1,1-diphosphonic acid tetraethyl ester,
or a pharmaceutically acceptable salt thereof, or any hydrate thereof, (for the manufacture of a pharmaceutical composition) for the treatment of fractures.

Administration of said methanebisphosphonic acid derivatives will benefit all mammals including man with fractures of any bone, especially vertebra, femur or radius.

The present invention is expected to have far reaching clinical and financial implications for the management of fractures. Treatment with said methanebisphosphonic acid derivatives promotes callus formation and fracture union, reducing the time required for mechanical fixation, thus allowing earlier mobilization and weight-bearing. This shorter immobilization time will result in considerable reductions in secondary complications (e.g. reflex sympathetic algodystrophy, tibial non-union, reduced risk of pulmonary embolism, muscle wasting and further bone loss secondary to immobilization) to produce enormous medical and economical benefit.

Thus, "treatment of fractures" means, in particular, promoting fracture healing, and, furthermore, improving the mechanical stability of the healing fracture.

Such fractures may be, for example, (a) the common, traumatic (disabling and non-osteoporotic) fractures, (b) the osteoporotic fractures (which are due to osteoporosis or osteopenia of any etiology), (c) fractures due to Paget's disease or (d) iatrogenic fractures.

"Iatrogenic fractures" means fractures due to bone loss as a consequence of side effects of other drugs, e.g. in asthma patients receiving high doses of corticosteroids.

In a particular embodiment of the invention, said methanebisphosphonic acid derivatives can be used to treat the common, traumatic fractures, the osteoporotic fractures or the iatrogenic fractures.

The osteoporotic fractures have—with increased ageing of the population—become a major health-care problem. More than 40% of women will suffer fracture of the spine, hip or wrist by the age of 70. Each year in the USA there are 1.2 billion osteoporotic fractures costing an estimated $10 billion per year, of which $6 billion alone is due to hip fractures (250,000 cases per year). In the elderly these fractures are often slow to heal and cause prolonged functional disability. Half the patients are unable to walk unaided and one quarter require long-term nursing care. Towards the end of their lives, ⅓ of women and ⅙ of men will have suffered a hip fracture, leading to death in 12–20% of cases. In view of this immense problem of morbidity and mortality associated with osteoporotic fractures, pharmaceutical agents which serve to improve fracture healing will be a major therapeutic advance.

In another embodiment of the invention, said methanebisphosphonic acid derivatives can be used to treat the common, traumatic fractures.

In a further embodiment of the invention, said methanebisphosphonic acid derivatives can be used to treat all fractures in mammals which are not suffering from Paget's disease.

In just another embodiment of the invention, said methanebisphosphonic acid derivatives can be used to treat all fractures in mammals which are not suffering from Paget's disease or osteoporosis.

The beneficial properties of the methanebisphonic acid derivatives according to the invention can be demonstrated, for example, in a fracture model where the effect of the active substance on the healing of a 3 mm osteotomy gap in the mid-diaphysis of the ovine tibia is evaluated using the model of fracture repair under rigid unilateral fixation of Goodship and Kenwright [J. Bone Joint Surgery 67B (1985) 650–655]. In this model, twelve skeletally mature adult female Welsh Mule sheep of body mass 60–70 kg are divided randomly into two groups of six. The animals are housed in large indoor pens under a fixed day length of 18 hours light to suppress the oestrus cycle. The experimental group is given, for example, 0.5 mg/ks of active substance in 250 ml saline as a slow intravenous infusion over a period of one hour once a week for four weeks prior to osteotomy and twelve weeks postoperatively. The control group is oiven a similar infusion of saline alone at identical intervals.

At weekly intervals throughout the twelve week healing period the repair process is evaluated by standard view radiographs, dual photon densitometry scan through the mid-point of the fracture gap and measurement of an index of fracture stiffness during walking from simultaneous measurement of deformation of the fixator bar and vertical ground reaction force.

At the end of the twelve week peiiod the animals are killed and the tibiae dissected free from soft tissues. Both the experimental and contralateral tibiae are mounted in a standard manner for torsional testing to determine torsional stiffness and ultimate torsional strength.

The results obtained can be summarized as follows: (1) Radiography: in all cases a more prolific callus is observed in the treated group. (2) Dual photon absoriptiometry: an increase in bone mineral content as a function of time occurs in both groups. The rate of increase is e.g. 76% greater in the treated group than the controls [on analysis of covariance, significant at the level of $p<0.01$]. (3) In vivo fracture stiffness: the values of fracture stiffness increase in magnitude as a function of time in both groups. However, no significant differences are found in either the rate of increase or end values between the two groups. (4) Post-mortem fracture stiffness: no significant increase in torsional stiffness is found using one tailed independent t-tests either between the treated and control osteotomies or between the intact contralateral tibiae. (5) Post-mortem torsional strength: a significantly greater ultimate torsional strength is found in the osteotomies of the treated group [$p<0.05$]; no differences are found between the intact contralateral bones of the two groups.

Pharmaceutically acceptable salts of a compound of formula I are preferably salts thereof with bases, conveniently metal salts derived from groups Ia, Ib, Ia and IIb of the Periodic Table of the Elements, including alkali metal salts, e.g. potassium and especially sodium salts, or alkaline earth metal salts, preferably calcium or magnesium salts, and also ammonium salts with ammonia or organic amines.

Substituted phenyl is mono- or polysubstituted, for example di- or trisubstituted, e.g. by lower alkyl, lower alkoxy, trifluoromiiethyl and/or preferably halogen.

Monocyclic 5- or 6-memiibered monoaza-aryl, diaza-aryl or thiaza-aryl is e.g. pyrrolyl, imidazolyl, including 1-, 2-, 4- or 5-imidazolyl, pyrazolyl such as 1- or 3-pyrazolyl, thiazolyl such as 2- or 4-thiazolyl, pyyridyl such as 2-, 3- or 4-pyridyl. Corresponding radicals can be substituted by one or more than one, e.g. by two or three, of e.g. alkyl group(s). Preferred substituted radicals include alkyl-substituted 1-imidazolyl and 5-imidazolyl, 5-lower alkyl-2-thiazolyl such as 5-methyl-2-thiazolyl, 5-ethyl-2-thiazolyl and 5-n-butyl-2-thiazolyl, as well as alkyl-substituted 2- and 3-pyridyl.

Unsubstitulted or substituted monocyclic 5- or 6-membered monoaza-aryl, diaza-aryl or thiaza-aryl which is bound throLugh a ring, carbon atoms is preferably a radical selected from the group consisting of 2-, 4- or 5-imidazolyl, 3-pyrazolyl, thiazolyl, e. 2- or 4-thiazolyl, and pyridyl, e.g. 2-, 3- or 4-pyridyl, and which is unsubstituted or substituted by lower alkyl.

Unsubstituted or substituted nionocyclic 5- or 6-membered monoaza-aryl, diaza-aryl or thiaza-aryl which is bound through a ring carbon atom or a ring nitrogen atom is preferably a radical selected from the group consisting of pyrrolyl, imidazolyl, pyrazolyl, thiazolyl or pyridyl which is unsubstituted or substituted by lower alkyl.

Unsubstituted or substituted bicyclic monoaza-, diaza- or triaza-aryl which is bound through a ring carbon atom or a ring nitrogen atom is e.g. imidazo[1,2-a]pyridyl, such as imidazo[1,2-a]pyridin-3-yl.

Alkyl is preferably lower alkyl, alkylene is preferably lower alkylene, and Ar-alkyl is e.g. phenyl-lower alkyl which may be substituted in the phenyl nucleus as indicated above.

Cycloalkyl is preferably $C_3$–$C_7$cycloalkyl, e.g. cyclopropyl, cyclobutyl, cyclopentyl, cyclohexyl or cycloheptyl.

Amino which is mono- or disubstituted by alkyl, cycloalkyl, Ar-alkyl, Ar—O-alkyl, Ar—S-alkyl or $Het_1$-alkyl is preferably lower alkylamino, $C_3$–$C_7$cycloalkylamino, phenyl-lower alkylamino, di-lower alkylamino, lower alkyl-phenyl-lower alkylamino, diphenyl-lower alkylamino, phenoxy-lower alkylamino, lower alkylphenoxy-lower alkylamino, phenoxy-lower alkylphenyl-lower alkylamino, diphenoxy-lower alkylamino, phenylthio-lower alkylamino, lower alkylphenylthio-lower alkylamino, phenylthio-lower alkylaminophenyl-lower alkylamino, diphenylthio-lower alkylamino, lower alkylpyridyl-lower alkylamino, phenyl-lower alkylpyridyl-lower alkylamino, phenoxy-lower alkylpyridyl-lower alkylamino, phenylthio-lower alkylpyridyl-lower alkylamino or dipyridyl-lower alkylamino, the phenyl or pyridyl moiety of which radicals may be substituted as indicated above.

Unsubstituted or Ar-substituted alkyleneamino is prelerably lower alkyleneamino, e.g. 1,4-butyleneamino (=pyrrolidin-1-yl) or 1,5-pentyleneamino (=piperidin-1-yl), or lower alkyleneamino which is substituted by a phenyl radical which is uinsubstituted or substituted as indicated above, e.g. 2-(4-chlorophenyl)-1,4-butyleneamino or 3-phenyl-1,5-penLyleneamino.

Alkyleneamino in which two alkylene carbon atoms are additionally linked to each other through alkylene is preferably lower alkyleneamino wherein two, preferably nonadjacent, lower alkylene carbon atoms are linked to each other through lower alkylene, in particular methylene. Corresponding 3-azabicyclo-$C_6$–$C_{10}$alk-3-yl radicals are preferred.

The general definitions cited above have the following preferred meanings, unless otherwise defined.

Halogen is e.g. fluoro or bromo, preferably chloro, but may also be iodo.

Lower alkyl is e.g. methyl, ethyl, n-propyl, isopropyl, n-butyl, isobutyl, sec- and tert-butyl, and in addition embraces corresponding pentyl, hexyl and heptyl radicals. $C_1$–$C_4$Alkyl is preferred.

Lower alkoxy is e.g. methoxy, ethoxy, n-propoxy, isopropoxy and n-butoxy and in addition embraces corresponding pentoxy, hexoxy and heptoxy radials. $C_1$–$C_4$Alkoxy is preferred.

Lower alkylene is straight-chain or branched and is e.g. $C_1$–$C_7$alkylene such as methylene, ethylene, propylene, butylene, pentylene, and also hexylene and heptylene, as well as e.g. 2-methyl-1,3-propylene, 2,4- or 1,5-dimethyl-1,5-pentylene. Lower alkylene as substituent of disubstituted amino $R_3$ contains at least two carbon atoms, preferably 4 to 6 carbon atoms. Lower alkylene which links together two lower alkylene carbon atoms of amino which is disubstituted by lower alkylene contains preferably up to 5 carbon atoms inclusive, and is preferably methylene.

$C_1$–$C_3$Alkyl is methyl, ethyl, n-propyl and isopropyl.

N-Phenylthiocarbamoyl is the group —C(=S)—$NHC_6H_5$.

Radicals or compounds qualified by the term "lower" contain up to 7 carbon atoms inclusive, preferably Lip to 4 carbon atoms inclusive.

The pharmaceutically useful methanebisphosphonic acid derivatives mentioned above are known or can be prepared in a manner known per se.

Thus, for example, compounds of formula 1, wherein $R_1$ is hydrogen and $R_2$ is Ar—S—, are obtainable by reacting tetra-lower alkyl methanebisphosphonate in the presence of a strong metal base such as NaH, with a disulfide of formula Ar—S—S—Ar and subsequent acid hydrolysis of the tetra-lower alkyl ester (q.v. inter alia EP-A-100 718).

Corresponding compounds of formula 1, wherein $R_1$ is hydrogen and $R_2$ is $Het_1$—NH—, may be e.g. prepared by reacting a mixture of $H_3PO_3$ and $PHal_3$, wherein Hal is halogen, preferably chloro, with a formylamine of formula $Het_1$—NH—CHO, or by heating an amine $Het_1$—$NH_2$ with a lower alkyl orthoformate and a di-lower alkyl phosphite and hydrolysing the reaction product, conveniently in the presence of an acid (q.v. inter alia EP-A-274 346).

Compounds of formula I, wherein $R_1$ is hydrogen and $R_2$ is —A—$R_3$, and A is alkylene, may be prepared by starting from compounds of formula $R_3$—A-Hal and reacting these with a tetra-lower alkyl methanebisphosphonate in the presence of a strong base, e.g. NaH, and hydrolysing the resultant tetra-lower alkyl esters of corresponding compounds of formuila I, conveniently in the presence of an acid such as hydrochloric acid (q.v. inter alia EP-A-275 821).

Compounds of formula 1, wherein $R_1$ is hydroxy and $R_2$ is —A—$R_3$, may e.g. be prepared by reacting a carboxylic acid of formula $R_2$—COOH with a phosphorylating agent, as with a mixture of $H_3PO_3$ and $PHal_3$, and working up the reaction product under hydrolytic conditions (q.v. inter alia EP-A-170 228 and EP-A-252 505).

The preparation of compounds of formula Ia (q.v. below) and pharimaceutically acceptable salts thereof is disclosed, inter alia, in DE-OS-2 405 254.

The preparation of compounds of formula I wherein $R_1$ is hydrogen and $R_2$ is N-phenylthiocarbamoyl is disclosed e.g. in EP-A-243 173.

The preparation of compounds of formula I wherein $R_1$ is hydrogen and $R_2$ is a group
  Ar—S—A—N(R')— or $Hcet_3$—S—A—N(R')— is disclosed e.;. in EP-A-464 509.

The invention relates in particular to the use of a methanebisphosphonic acid derivative of formula I, wherein
  (a) $R_1$ and $R_2$ are each independently of the other halogen, or
  (b) $R_1$ is hydrogen and $R_2$ is a group Ar—S—, $Het_1$—NH—, Cyc—NH—, Ar—S—A—NH—, $Het_3$—S—A—NH— or is N-phenylthiocarbamoyl, wherein Ar is unsubstituted phenyl or phenyl which is substituted by lower alkyl, lower alkoxy, trifluoromethyl and/or halogen, $Het_1$ is unsubstituted thiazolyl or thiazolyl which is substituted by lower alkyl, Cyc is $C_3$–$C_7$cycloalkyl, A is lower alkylene and $Het_3$ is thiazolyl or pyridyl, which are each unsubstituted or substituted by lower alkyl, or
  (c) $R_1$ is hydrogen or hydroxy and $R_2$ is —A—$R_3$, wherein A is lower alkylene, and
  $R_3$ is either unsubstituted or lower alkyl-substituted imidazolyl which is bound through a ring carbon atom or a ring nitrogen atom, or is pyridyl, or
  $R_3$ is imidazo[1,2-a]pyridyl, or
  $R_3$ is unsubstituted amino or amino which is mono- or disubstituted by lower alkyl, $C_3$–$C_7$cycloalkyl, Ar-lower alkyl, Ar—O-lower alkyl, Ar—S-lower alkyl or pyridyl-lower alkyl, each independently of one another, and Ar is as defined above, or
  $R_3$ is unsubstituted or Ar-substituted $C_4$–$C_6$alkyleneamino, wherein two non-adjacent lower alkylene carbon atoms may be additionally linked to each other through $C_1$–$C_3$alkylene, and Ar is as defined above,
or of the methanebisphosplhonic acid esters 5-benzoyl-3,4-dihydro-2H-pyrazole-3,3-diphosphonic acid tetraethiyl ester or 1-(4-phenyltliiobutylamino)methane-1,1-diphosphonic acid tetraethyl ester,
or a pharmaceutically acceptable salt thereof, or any hydrate thereof, (for the manufacture of a pharmaceutical composition) for the treatment of fractures.

The invention relates more particularly to the use of a methanebisphosphonic acid of formula I, wherein
  (a) $R_1$ and $R_2$ are halogen, or
  (b) $R_1$ is hydrogen and $R_2$ is unsubstituted or halogen-substituted phenylthio, unsubstituted or lower alkyl-substituted thiazolylamino, $C_5$–$C_7$cycloalkylamino, or is N-phenylthiocarbamoyl, or
  (c) $R_1$ is hydrogen or hydroxy and $R_2$ is —A—$R_3$, wherein A is $C_1$–$C_7$alkylene and $R_3$ is an unsubstituted or lower alkyl-substituted irnidazolyl radical which is bound through a ring carbon atom or a ring nitrogen atom, or is pyridyl, or is imidazo[1,2-a]pyridyl, or
  (d) $R_1$ is hydroxy and $R_2$ is —A—$R_3$, wherein A is $C_1$–$C_7$alkylene und $R_3$ is amino, di-$C_1$–$C_5$alkylamino, N-$C_3$–$C_7$cycloalkylamino, N-$C_1$–$C_4$alkyl-N-phenyl-$C_1$–$C_5$alkylamino, N-$C_1$–$C_4$alkyl-N-phenoxy-$C_1$–$C_4$alkyl, N-$C_1$–$C_4$alkyl-N-phenylthio-$C_1$–$C_4$alkyl, N-$C_1$–$C_4$alkyl-N-pyridyl-$C_1$–$C_4$alkylamino; $C_4$–$C_6$alkyleneamino which is unsubstituted or substituted by phenyl which is in turn unsubstituted or substituted by halogen; or 1,5-di-$C_1$–$C_4$alkyl-3-azabicyclo[3.1.1]hept-3-yl,
or of the methanebisphosphonic acid esters 5-benzoyl-3,4-dihydro-2H-pyrazole-3,3-diphosphonic acid tetraethyl ester or 1-(4-phenylthiobutylamino)methane-1,1-diphosphonic acid tetraethyl ester,
or a pharmaceutically acceptable salt thereof, or any hydrate thereof, (for the manufacture of a pharmaceutical composition) for the treatment of fractures.

The invention relates preferably to the use of a methanebisphosphonic acid of formula I, wherein (a) $R_1$ and $R_2$ are chloro, or (b) $R_1$ is hydrogen and $R_2$ is unsubstituted or chloro-substituted phenylthio, unsubstituted or $C_1$–$C_4$alkyl-substituted thiazolylamino, cycloheptylamino, or is N-phenylthiocarbamoyl, or (c) $R_1$ is hydroenl or hyd(roxy and $R_2$ is —A—$R_3$, wherein A is methylene, ethylene, propylene or pentylene, and $R_3$ is imnidazol-1-yl, imidazol-5-yl, 1-methylimidazol-2-yl, 4-methylimiidazol-5-yl, 2- or 3-pyridyl, or imidazo[1,2-a]pyridin-3-yl, or (d) $R_1$ is hydroxy and $R_2$ is —A—$R_3$, wherein A is methylene, ethylene, propylene or pentylene, and $R_3$ is amino, dimethylamino, N-methyl-N-n-propylamino, N-methyl-N-n-pentylamino, N-cycloheptylamnino, N-methyl-N-(2-phenylethyl)amino, N-methyl-N-(3-phenylpropyl)amino or N-methyl-N-(5-phenylpentyl)amino, N-methyl-N-(3-phenoxyprupyl)amino, N-methyl-N-(2-phenylLhioethyl)amino, N-methyl-N-(3-phenylthiopropyl)amino, N-methyl-N-[3-(2-pyridyl)propyl]amino, piperidin-1-yl, which is unsubstituted or substituted in 4-position by phenyl, or pyrrolidin-1-yl, which is unsubstituted or substituted in 3-position by 4-chlorophenyl, or is 1,5-dimethyl-3-azabicyclo[3.1.1]hept-3-yl, or of the methanebisphosphonic acid esters 5-benzoyl-3,4-dihydro-2H-pyrazole-3,3-diphosphonic acid tetraethyl ester or 1-(4-phenylthiobutylamino)methane-1,1-diphosphonic acid tetraethyl ester, or a pharmaceutically acceptable salt thereof, or any hydrate thereof, (for the manufacture of a pharmaceutical composition) for the treatment of fractures.

The invention relates very particularly to the use of a methanebisphosphonic acid selected from the followin group of compounds of formula I:

4-amino-1-hydroxybutane-1,1-diphosphonic acid, 6-amino-1-hydroxyhexane-1,1-diphosphonic acid, 3-(N-methyl-N-n-pentylamino)-1-hydroxypropane-1,1-diphosphonic acid, 3-[N-(3-phenylpropyl)-N-methylamino]-1-hydroxypropane-1,1-diphosphonic acid, 3-(N-methyl-N-5-plienylpentylamino)-1-hydroxypropane-1,1-diphosphonic acid, 3-[N-methyl-N-3-(2-pyridyl)propylamino]-1-hydroxypropane-1,1-diphosphonic acid, 1-hydroxy-3-[N-methyl-N-(3-phenoxypropyl)amino]propane-1,1-diphosphonic acid, 1-hydroxy-3-[N-melhyl-N-(2-phenoxyethyl)amino]propane-1,1-diphosphonic acid, 4-(4-phenylpiperidin-1-yl)-1-hydroxybutane-1,1-diphosphonic acid, 1-hydroxy-3-(1-piperidino)propane-1,1-diphosphonic acid, 1-hydroxy-3-[3-(4-chlorophenyl)pyrrolidin-1-yl]propane-1,1-diphosphonic acid, 1-hydroxy-2-(imidazol-1-yl)ethane-1,1-diphosphonic acid, 2-(1-methylimnidazol-2-yl)ethane-1,1-diphosphonic acid, 1-hydroxy-2-(4-methylimidazol-5-yl)ethane-1,1-diphosphonic acid, 1-hydroxy-2-(imidazol-5-yl)ethane-1,1-diphosphonic acid, 1-hydroxy-2-(3-pyyridyl)ethane-1,1-diphosphonic acid, 2-(2-pyridyl)ethane-1,1-diphosphonic acid, 1-[(5-n-butyl-2-thiazolyl)amino]methane-1,1-diplhosphonic acid, 1-[(5-methyl-2-thiazolyl)amino]methane-1,1-diphosphonic acid, 1-[(2-thiazolyl)amino]-methane-1,1-diphosphonic acid, 1-(4-chlorophenylthio)methane-1,1-diphosphonic acid, 1,1-dichloromethane-1,1-diphosphonic acid, 3-(1,5-dimethyl-3-azabicyclo[3.1.1]hept-3-yl)-1-hydroxypropane-1,1-diphosphonic acid, 1-[(5-ethyl-2-thiazolyl)amino]methane-1,1-diphosphonic acid, 3-[N-(2-phenylethyl)-N-methylamino]-1-hydroxypropane-1,1-diphosphonic acid, 3-[N-(2-phenylthioethyl)-N-methylamino]-1-hydroxypropane-1,1-diphosphonic acid, 3-[N-(3-phenylthiopropyl)-N-methylarnino]-1-hydroxypropane-1,1-diphosphonic acid, 1-hydroxy-3-(pyrrolidin-1-yl)propane-1,1-diphosphonic acid, 1-(N-cycloheptylamino)methane-1,1-diphosphonic acid, 2-(N,N-dimethylamino)-1-hydroxyethane-1,1-diphosphonic acid, 3-amino-1-hydroxypropane-1,1-diphosphonic acid, 3-(N,N-dimethylamino)-1-hydroxypropane-1,1-diphosphonic acid, 3-(N-methyl-N-n-propylamino)-1-hydroxypropane-1,1-diphosphonic acid, 1-[N-(4-phenylthiobutyl)-amino]methane-1,1-diphosphonic acid, 1-{N-[4-(2-pyridyl)thiobutyl]amino}methane-1,1-diphosphonic acid, 1-(N-phenylaminothiocarbonyl)methane-1,1-diphosphonic acid, 5-benzoyl-3,4-dihydro-2H-pyrazole-3,3-diphosphonic acid tetraethyl ester, 1-(4-phenylthiobutylamino)methane-1,1-diphosphonic acid tetraethyl ester, 1-hydroxy-2-(imidazo[1,2-a]pyridin-3-yl)ethane-1,1-diphosphonic acid, or a pharmaceutically acceptable salt thereof, or any hydrate thereof.

A particular embodiment of the invention is represented by the use of a methanebisphosphonic acid derivative, or a pharmaceutically acceptable salt thereof, or any hydrate thereof, which is selected from 4-amino-1-hydroxybutane-1,1-diphosphonic acid, e.g. alendronate; 6-amino-1-hydroxyhexane-1,1-diphosphonic acid, e.g. amino-hexyl-BP; 3-(N-methyl-N-n-pentylamino)-1-hydroxypropane-1,1-diphosphonic acid, e.g. methyl-pentyl-APD (=BM 21.0955); 1-hydroxy-2-(imidazol-1-yl)ethane-1,1-diphosphonic acid; 1-hydroxy-2-(3-pyridyl)ethane-1,1-diphosphonic acid, e.g. risedronate; 1-(4-chlorophenylthio)methane-1,1-diphosphonic acid, e.g. tiludronate; 1,1-dichloromethane-1,1-diphosphlonic acid, e.g. clodronate; 3-[N-(2-plhenylthioethyl)-N-methylamino]-1-hydroxypropaane-1,1-diphosphonic acid; 1-hydroxy-3-(pyrrolidin-1-yl)-propane-1,1-diphosphonic acid, e.g. EB 1053 (Leo); 1-(N-cycloheptylamino)methane-1,1-diphosphonic acid, e.g. YM 175; 3-amino-1-hydroxypropane-1,1-diphosphonic acid, e.g. disodium pamitdronate; 3-(N,N-dimethylamino)-1-hydroxypiopane-1,1-diphosphonic acid, e.g. dimethlyl-APD; 1-(N-phenylaminothiocarbonyl)methane-1,1-diphosphonic acid, e.g. FR 78844 (Fujisawa); 5-benzoyl-3,4-dihydro-2H-pyrazole-3,3-diphosphonic acid tetraethyl ester, e.g. U-81581 (Upjohn); 1-(4-phenylthiobtltylamino) miiethane-1,1-diphosphonic acid tetraethyl ester; and 1-hydroxy-2-(imidazo[1,2-a]pyridin-3-yl)ethane-1,1-diphlosphoniic acid, e.g. YM 529.

Another embodiment of the invention is represented by the use of a methanebisphosphonic acid derivative, or a pharmaceutically acceptable salt thereof, or any hydrate thereof, which is selected from AJ-704 and BBR-2756.

The invention relates especially to the use of a methanebisphosphonic acid derivative a compound of formula Ia

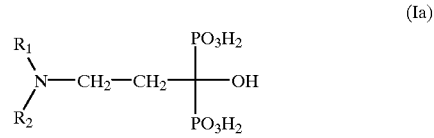

(Ia)

wherein $R_1$ and $R_2$ are each independently of the other hydrogen or $C_1$–$C_3$alkyl, or a pharmaceutically acceptable salt thereof, or any hydrate thereof, (for the manufacture of a pharmaceutical composition) for the treatment of fractures.

The invention relates first and foremost to the use of the disodium salt of 3-amino-1-hydroxypropane-1,1-diphosphonic acid—hereinafter called disodium pamidronate—(for the manufacture of a pharmaceutical composition) for the treatment of fractures.

The pharmaceutically useful methaniebisphosphonic acid derivatives may be used in the form of a possible isomer or of a mixture of isomers, typically as optical isomers such as enantiomers or diastereoisomers or geometric isomers, typically cis-trans isomers. The optical isomers are obtained in the form of the puic antipodes and/or as racemates.

The pharmaceutically useful methanebisphosphlonic acid derivatives can also be used in the form of their hydrates or include other solvents used for their crystallisation.

The methanebisphosphonic acid derivative is preferably used in the form of a pharmaceutical preparation that contains a therapeutically effective amount of the active ingredient optionally together with or in admixture with inorganic or organic, solid or liquid, pharmaceutically acceptable carriers which are suitable for administration.

The pharmaceutical compositions may be, for example, compositions for enteral, such as oral, rectal or nasal administration, compositions for parenteral, such as intravenous or subcutaneous administration, or compositions for transdermal administration (e.g. passive or iontophoretic). Furthermore, direct local administration at the fracture site comes into consideration.

The particular mode of administration and the dosage will be selected by the attending physician taking into account the particulars of the patient, the fracture and the fracture state involved.

The dosage of the active ingredient may depend on various factors, such as effectiveness and duration of action of the active ingredient, mode of administration, warm-blooded species, and/or sex, age, weight and individual condition of the warm-blooded animal.

The approximate daily dosage normally to be recommended for a warm-blooded animal weighing approximately 75 kg is of from 0.01 up to 100 mg/kg, preferably of from 0.10 up to 5 mg/kg, especially of from 0.12 up to 5 mg/kg, which is optionally taken in several, optionally equal, partial doses. But also other, e.g. weekly regimens, for example 0.01 up to 100 mg/kg, preferably of from 0.10 up to 5 mg/kg, especially of from 0.12 up to 5 mg/kg, once, twice or thrice weekly, come into consideration.

Preferably, the methanebisphosphonic acid derivatives are administered in doses which are in the same order of magnitude as those used in the treatment of the diseases classically treated with methanebisphosphonic acid derivatives, such as Paget's disease, tumour-induced hypercalcaemia or osteoporosis. In other words, preferably the methanebisphosphonic acid derivatives are administered in doses which would likewise be therapeutically effective in the treatment of Paget's disease, tumour-induced hypercalcaemia or osteoporosis, i.e. preferably they are administered in doses which would likewise effectively inhibit bone resorption.

Formulations in single dose unit form contain preferably from about 1% to about 90%, and formulations not in single dose unit form contain preferably from about 0.1% to about 20%, of the active ingredient. Single dose unit forms such as capsules, tablets or dragees contain e.g. from about 1 mg to about 500 mg of the active ingredient.

In the case of 3-amino-1-hydrioxypropane-1,1-diphosphonic acid, or a pharmaceutically acceptable salt thereof, especially disodillmll pamidronate, or any hydrate thereof, preferably a dose of 0.15–4.90 mg/kg, especially 0.30–3.40 mg/kg—in several paltial doses or advantageously as a single dose—is administered to the mammal in need thereof, preferably within 7 days after fixation of the fracture. Optionally, another dose of 0.15–4.90 mg/kg, especially 0.30–3.40 mg/kg—in several partial doses or advantageously as a single dose—is administered to the mammnal, preferably within the next 30 days after administration of the first dose. Preferred is the direct local administration at the fracture site or intravenous administration of disodium pamidronate.

"mg/kg" means mg drug per kg body weight of the mammal to be treated.

In each of the cases of (a) 4-amino-1-hydroxybutane-1,1-diphosphonic acid, (b) 6-amino-1-hydroxyhexane-1,1-diphosphonic acid, (c) 3-(N-methyl-N-n-pentylamino)-1-hydroxypropane-1,1-diphosphonic acid, (d) 1-hydroxy-2-(imidazol-1-yl)-ethane-1,1-diphosphonic acid, (e) 1-hydroxy-2-(3-pyridyl)ethane-1,1-diphosphonic acid, (t) 1-(4-chlorophenylthio)methane-1,1-diphosphonic acid, (g) 3-[N-(2-phenylthioethyl)-N-methylamino]-1-hydroxypropane-1,1-diphosphonic acid, (h) 1-hydroxy-3-(pyrrolidin-1-yl)propane-1,1-diphosphonic acid, (i) 3-(N,N-dimethylamino)-1-hydroxypropane-1,1-diphosphonic acid, (i) 1-(N-phenylaminothiocarbonyl)methane-1,1-diphosphonic acid, (k) 5-benzoyl-3,4-dihydro-2H-pyrazole-3,3-diphosphonic acid tetraethyl ester, (1) 1-(4-phenylthiobuLtylamino)methane-1,1-diphosphonic acid tetraethyl ester and (m) 1-hydroxy-2-(i1idazo[1,2-a]pyridin-3-yl)ethane-1,1-diphosphonic acid, or a pharmaceutically acceptable salt thereof, or any hydrate thereof, preferably a dose of 0.01–3.40 mg/kg, especially 0.05–2.40 mg/kg—in several partial doses or advantageously as a single dose—is administered to the mammiiiial in need thereof, preferably within 7 days after fixation of the fracture. Optionally, aniother dose of 0.01–3.40 mg/kg, especially 0.05–2.40 mg/kg—in several partial doses or advantageously as a single dose—is administered to the mammal, preferably within the next 30 days after administration of the first dose. Preferred is the direct local administration at the fracture site or intravenous administration of any of the drugs mentioned above.

The invention further relates to the use of a composition for the manufacture of a medicament, e.g. in single dose unit form, for the treatment of fractures in mammals, wherein the composition contains 0.15–4.90 mg/kg, especially 0.30–3.40 mg/kg, of 3-amino-1-hydroxypropane-1,1-diphiosphoiiic acid, or a pharmaceutically acceptable salt thereof, especially disodium pamidronate, or any hydrate thereof, per dosae form.

Moreover, the invention relates to the use of 3-amino-1-hydroxypropane-1,1-diphosphonic acid, or a plhawmaceutically acceptable salt thereof, especially disodium pamidronate, or any hydrate thereof, at a dose of 0.15–4.90 mg/kg, especially 0.30–3.40 mg/kg, per dosage form for the manufacture of a medicament for the treatment of fractures.

The invention further relates to the use of a composition for the manufacture of a medicament, e.g. in single dose unit form, for the treatment of fractures in mammals, wherein the composition contains 0.01–3.40 mglkg, especially 0.05–2.40 mg/kg, of a compound selected from (a) 4-amino-1-hydroxybutane-1,1-diphosphonic acid, (b) 6-amino-1-hydroxyhexane-1,1-diphosphonic acid, (c) 3-(N-methyl-N-n-pentylamino)-1-hydroxypropane-1,1-diphosphonic acid, (d) 1-hydroxy-2-(imidazol-1-yl)-ethane-1,1-diphosphonic acid, (e) 1-hydroxy-2-(3-pyridyl)ethane-1,1-diphosphonic acid, (f) 1-(4-chlorophenylthio)methane-1,1-diphosphonic acid, (g) 3-[N-(2-phenylthioethyl)-N-methylamino]-1- hydroxypropane-1,1-diphosphonic acid, (h) 1-hydroxy-3-(pyrrolidin-1-yl)propane-1,1-diphosphonic acid, (i) 3-(N,N-dimethylamino)-1-hydroxypropane-1,1-diphosphonic acid, (i) 1-(N-phenylaminothiocarbonyl)methane-1,1-diphosphonic acid, (k) 5-benzoyl-3,4-dihydro-2H-pyrazole-3,3-diphosphonic acid tetraethyl ester, (1) 1-(4-phenylthiobutylaniino)methane-1,1-diphosphonic acid tetraethyl ester and (ni) 1-hydroxy-2-(imidazo[1,2-a]pyridin-3-yl)ethane-1,1-diphosphonic acid, and pharmaceutically acceptable salts thereof, and any hydrate thereof, per dosage form.

Moreover, the invention relates to the use of a compound selected from (a) 4-amino-1-hydroxybutane-1,1-diphosphonic acid, (b) 6-amino-1-hydroxyhexane-1,1-diphosphonic acid, (c) 3-(N-methyl-N-n-pentylamino)-1-hydroxypropane-1,1-diphosphonic acid, (d) 1-hydroxy-2-(imidazol-1-yl)ethane-1,1-diphosphonic acid, (e) 1-hydroxy-2-(3-pyridyl)ethatine-1,1-diphosphonic acid, (f) 1-(4-chlor(ophenyltliio)methane-1,1-diphosphonic acid, (g) 3-[N-(2-plhenylthioetliyl)-N-methylaminio]-1-hydroxypiopantie-1,1-diphosphonic acid, (h) 1-hydroxy-3-(pyi-rolidin-1-yl)propane-1,1-diplhosphonic acid, (i) 3-(N,N-dimeLhylamino)-1-hydroxypropane-1,1-diphosphonic acid, (i) 1-(N-phenylaminothiocarbonyl)methane-1,1-diphiosphonic acid, (k) 5-benzoyl-3,4-dihydro-2H-pyrazole-3,3-diphosphonic acid tetraethyl ester, (1) 1-(4-phenylthiobutylamino)methane-1,1-diphosphonic acid telraethyl ester and (m) 1-hydroxy-2-(imidazo[1,2-a]pyridin-3-yl)ethane-1,1-diphosphonic acid, and pharmaceutically acceptable salts thereof, and any hydrate thereof, at a dose of 0.01–3.40 mg/kg, especially 0.05–2.40 mg/kg, per dosage form for the manufacture of a medicament for the treatment of fractures.

Pharmaceutical preparations for enteral and parenteral administration are, for example, those in dosage unit forms, such as dragees, tablets or capsules and also ampoules. They are prepared in a manner known per se, for example by means of conventional mixing, granulating, confectioning, dissolving or lyophilising processes. For example, pharmaceutical preparations for oral administration can be obtained by combining the active ingredient with solid carriers, where appropriate granulating a resulting mixture, and processing the mixture or granulate, if desired or necessary after the addition of suitable adjuncts, into tablets or dragee cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes, using, for example, corn, wheat, rice or potato starch, gelatin, tragacanth, methylcellulose and/or polyvinylpyrrolidone and, if desired, disintegrators, such as the above-mentioned starches, also carboxymethyl starch, crosslinked polyvinylpyrrolidone, agar or alginic acid or a salt thereof, such as sodium alginate. Adjuncts are especially flow-regulating agents and lubricants, for example silicic acid, talc, stearic acid or salts thereof, such as magnesium or calcium stearate, and/or polyethylene glycol. Drae cores are provided with suitable coatings that may be resistant to gasatic juices, there being used, inter alia, concentrated sugar solutions that optionally contain gum arabic, talc, polyvinylpyrrolidone, polyethylene glycol and/or titanium dioxide, or lacquer solutions in suitable organic solvents or solvent mixtures or, to produce coatings that are resistant to gastric juices, solutions of suitable cellulose preparations, such as acetylcellulose phthalate or hydroxypropylmethylcellulose phthalate. Colouring substances or pigments may be added to the tablets or drage coatings, for example for the purpose of identification or to indicate different doses of active ingredient.

Other orally administrable pharmaceutical preparations are dry-filled capsules made of gelatin, and also soft, sealed capsules made of gelatin and a plasticiser, such as glycerol or sor-bitol. The dry-filled capsules may contain the active ingredient in the form of a granulate, for example in admixture with fillers, such as lactose, binders, such as starches, and/or glidants, such as talc or malinesiumii stearate, and, where appropriate, stabilisers. In soft capsules the active ingredient is prefeiably dissolved or suspended in suitable liquids, such as fatty oils, par-afliin oil or liquid polyethylene glycols, it being possible also for stabilisers to be added.

Parenteral formulations are especially injectable fluids that are effective in various manners, such as intravenously, intramuscularly, intraperitoneally, intranasally, intradermally or subcutaneously. Such fluids are preferably isotonic aqueous solutions or suspensions which can be prepared before use, for example from lyophilised preparations which contain the active ingredient alone or together with a pharmaceutically acceptable carrier. The pharmaceutical preparations may be sterilised and/or contain adjuncts, for example preservatives, stabilisers, wetting agents and/or emulsifiers, solubilisers, salts for regulating the osmotic pressure and/or buffers.

Suitable formulations for transdermal application include an effective amount of the active ingredient with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the active ingredient of the skin of the host at a controlled and predetermined rate over a prolonged period of time, and means to secure the device to the skin.

The following Examples illustrate the invention described hereinbefore. The term "active ingredient" is to be understood as being any one of the methanebisphosphonic acid derivatives mentioned above as being useful according to the present invention.

EXAMPLE 1

Capsules containing coated pellets of, for example, disodium pamidlronate pentahydrate, as active ingredient:
Core Pellet:

| | |
|---|---|
| active ingredient (ground) (≙ 150 mg of anhydrous active ingredient) | 197.3 mg |
| Microcrystalline cellulose (Avicel ® PH 105) | 52.7 mg |
| | 250.0 mg |

+Inner Coating:

| | |
|---|---|
| Cellulose HP-M 603 | 10.0 mg |
| Polyethylene glycol | 2.0 mg |
| Talc | 8.0 mg |
| | 270.0 mg |

+Gastric Juice-resistant Outer Coating:

| | |
|---|---|
| Eudragit ® L 30 D (solid) | 90.0 mg |
| Triethyl citrate | 21.0 mg |
| Antifoam ® AF | 2.0 mg |
| Water | |
| Talc | 7.0 mg |
| | 390.0 mg |

A mixture of disodium pamidronate with Avicel® PH 105 is moistened with water and kneaded, extruded and formed into spheres. The dried pellets are then successively coated in the fluidized bed with an inner coating, consisting of cellulose HP-M 603, polyethylene glycol (PEG) 8000 and talc, and the aqueous gastric juice-resistant coat, consisting of Eudragit(® L 30 D, triethyl citrate and Antifoam® AF. The coated pellets are powdered with talc and filled into capsules (capsule size 0) by means of a commercial capsule filling machine, for example Höfliger and Karg.

EXAMPLE 2

Monolith adhesive transdermal system, containing as active ingredient, for example, 1-hydioxy-2-(imiildazol-1-yl)-ethane-1,1-diphosphonic acid:
Composition:

| | |
|---|---|
| polyisobutylene (PIB) 300 (Oppanol B1, BASF) | 5.0 g |
| PIB 35000 (Oppanol B10, BASF) | 3.0 g |
| PIB 1200000 (Oppanol B100, BASF) | 9.0 g |
| hydrogenated hydrocarbon resin (Escorez 5320, Exxon) | 43.0 g |
| 1-dodecylazacycloheptan-2-one (Azone, Nelson Res., Irvine/CA) | 20.0 g |
| active ingredient | 20.0 g |
| Total | 100.0 g |

Preparation:

The above components are together dissolved in 150 g of special boiling point petroleum fraction 100–125 by rolling on a roller gear bed. The solution is applied to a polyester film (Hostaphan, Kalle) by means of a spreading device using a 300 µm doctor blade, giving a coating of about 75 gm². After drying (15 minutes at 60° C.), a silicone-treated polyester film (thickness 75 µm, Laufenberg) is applied as the peel-off film. The finished systems are punched out in sizes in the wanted form of from 5 to 30 cm² using a punching tool. The complete systems are sealed individually in sachets of aluminised paper.

EXAMPLE 3

Ampoule containing disodium pamidronate pentahydrate dissolved in water. The solution (concentration 3 mg/ml) is for i.v. infusion after dilution.
Composition:

| | |
|---|---|
| active ingredient (= 15.0 mg of anhydrous active ingredient) | 19.73 mg |
| mannitol | 250 mg |
| water for injection | 5 ml. |

EXAMPLE 4

Tablets each containing 50 mg of 3-[N-(2-phenylthioethyl)-N-methylallmino]-1-hydroxypropane-1,1-diphosphonic acid can be prepared as follows:
Composition (10,000 tablets)

| | |
|---|---|
| Active ingredient | 500.0 g |
| Lactose | 500.0 g |
| Potato starch | 325.0 g |
| Gelatin | 8.0 g |
| Talc | 60.0 g |
| Magnesium stearate | 10.0 g |
| Silicon dioxide (finely divided) | 20.0 g |
| Ethanol | q.s. |

The active ingredient is mixed with the lactose and 292 g of potato starch, and the mixture is moistened with an ethanolic solution of the gelatin and granulated through a sieve. After the granules have dried, the remainder of the potato starch, the magnesium stearate and the silicon dioxide are admixed and the mixture compressed to give tablets each weighing 145.0 mg and containing 50.0 mg of active ingredient, which can, if desired, be provided with breaking grooves to enable the dosage to be more finely adjusted.

What is claimed is:

1. A method of treating fractures in mammals, which comprises administering to a mammal in need thereof a therapeutically effective amount of a compound of formula I

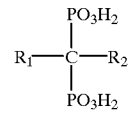

(I)

wherein
(a) $R_1$ and $R_2$ are each independently of the other halogen or
(b) $R_1$ is hydrogen and $R_2$ is a group Ar—S—, $Het_1$—NH—, Cyc—NH—, Ar—S—A—N(R')—, $Het_3$—S—A—N(R')— or is N-phenylthiocarbamoyl, wherein Ar is unsubstituted or substituted phenyl, $Het_1$ and $Het_3$ are each unsubstituted or substituted monocyclic 5- or 6-membered monoaza-, diaza- or thiaza-aryl which is bound through a ring carbon atom, Cyc is cycloalkyl, A is alkylene and R' is hydrogen or lower alkyl, or
(c) $R_1$ is hydrogen or hydroxy and $R_2$ is —A—$R_3$, wherein A is alkylene, and
$R_3$ is either Ar as defined above or is $Het_2$, which has the meaning of $Het_1$ but can be bound through a ring carbon atom or a ring nitrogen atom, or
$R_3$ is unsubstituted or substituted bicyclic monoaza-, diaza- or triaza-aryl which is bound through a ring carbon atom or a ring nitrogen atom, or
$R_3$ is unsubstituted amino or amino which is mono- or disubstituted by alkyl, cycloalkyl, Ar-alkyl, Ar—O— alkyl, Ar—S-alkyl or Het$_1$-alkyl each independently of one another, and Ar and Het$_1$ are as defined above, or R$_3$ is unsubstituted or Ar-substituted alkyleneamino, wherein two alkylene carbon atoms may be additionally linked to each other through alkylene, and Ar is as defined above, or of the methanebisphosphonic acid esters 5-benzoyl-3,4-dihydro-2H-pyrazole-3,3-diphosphonic acid tetraethyl ester or 1-(4-phenylthiobutylamino)methane-1,1-diphosphonic acid tetraethyl ester, or a pharmaceutically acceptable salt thereof, or any hydrate thereof.

2. A method according to claim 1, wherein the compound administered is a compound of formula I, wherein (a) R$_1$ and R$_2$ are each independently of the other halogen, or (b) R$_1$ is hydrogen and R$_2$ is a group Ar—S—, Het$_1$—NH—, Cyc—NH—, Ar—S—A—NH—, Het$_3$—S—A—NH— or is N-phenylthiocarbamoyl, wherein Ar is unsubstituted phenyl or phenyl which is substituted by lower alkyl, lower alkoxy, trifluoromethyl and/or halogen, Het$_1$ is unsubstituted thiazolyl or thiazolyl which is substituted by lower alkyl, Cyc is C$_3$–C$_7$cycloalkyl, A is lower alkylene and Het$_3$ is thiazolyl or pyridyl, which are each unsubstituted or substituted by lower alkyl, or (c) R$_1$ is hydrogen or hydroxy and R$_2$ is —A—R$_3$, wherein A is lower alkylene, and R$_3$ is either unsubstituted or lower alkyl-substituted imidazolyl which is bound through a ring carbon atom or a ring nitrogen atom, or is pyridyl, or R$_3$ is imidazo[1,2-a]pyridyl, or R$_3$ is unsubstituted amino or amino which is mono- or disubstituted by lower alkyl, C$_3$–C$_7$cycloalkyl, Ar-lower alkyl, Ar—O-lower alkyl, Ar—S-lower alkyl or pyridyl-lower alkyl, each independently of one another, and Ar is as defined above, or R$_3$ is unsubstituted or Ar-substituted C$_4$–C$_6$alkyleneamino, wherein two non-adjacent lower alkylene carbon atoms may be additionally linked to each other through C$_1$–C$_3$alkylene, and Ar is as defined above, or is one of the methanebisphosphonic acid esters 5-benzoyl-3,4-dihydro-2H-pyrazole-3,3-diphosphonic acid tetraethyl ester and 1-(4-phenylthiobutylamino)methane-1,1-diphosphonic acid tetraethyl ester, or a pharmaceutically acceptable salt thereof or any hydrate thereof.

3. A method according to claim 1, wherein the compound administered is a compound of formula I, wherein (a) R$_1$ and R$_2$ are halogen, or (b) R$_1$ is hydrogen and R$_2$ is unsubstituted or halogen-substituted phenylthio, unsubstituted or lower alkyl-substituted thiazolylamino, C$_5$–C$_7$cycloalkylamino, or is N-phenylthiocarbamoyl, or (c) R$_1$ is hydrogen or hydroxy and R$_2$ is —A—R$_3$, wherein A is C$_1$–C$_7$alkylene and R$_3$ is an unsubstituted or lower alkyl-substituted imidazolyl radical which is bound through a ring carbon atom or a ring nitrogen atom, or is pyridyl, or is imidazo[1,2-a]pyridyl, or (d) R$_1$ is hydroxy and R$_2$ is —A—R$_3$, wherein A is C$_1$–C$_7$alkylene und R$_3$ is amino, di-C$_1$–C$_5$alkylamiino, N-C$_3$–C$_7$cycloalkylamino, N-C$_1$–C$_4$alkyl-N-phenyl-C$_1$–C$_5$alkylamino, N-C$_1$–C$_4$alkyl-N-phenoxy-C$_1$–C$_4$alkyl, N-C$_1$–C$_4$alkyl-N-phenylthio-C$_1$–C$_4$alkyl, N-C$_1$–C$_4$alkyl-N-pyridyl-C$_1$–C$_4$alkylamino; C$_4$–C$_6$alkyleneamino which is unsubstituted or substituted by phenyl which is in turn unsubstituted or substituted by halogen; or 1,5-di-C$_1$–C$_4$alkyl-3-azabicyclo[3.1.1]hept-3-yl, or is one of the methanebisphosphonic acid esters 5-benzoyl-3,4-dihydro-2H-pyrazole-3,3-diphosphonic acid tetraethyl ester and 1-(4-phenylthiobutylamino)methane-1,1-diphosphonic acid tetraethyl ester, or a pharmaceutically acceptable salt thereof, or any hydrate thereof.

4. A method according to claim 1, wherein the compound administered is a compound of formula I, wherein (a) R$_1$ and R$_2$ are chloro, or (b) R$_1$ is hydrogen and R$_2$ is unsubstituted or chloro-substituted phenylthio, unsubstituted or C$_1$–C$_4$alkyl-substituted thiazolylamino, cycloheptylamino, or is N-phenylthiocarbamoyl, or (c) R$_1$ is hydrogen or hydroxy and R$_2$ is —A—R$_3$, wherein A is methylene, ethylene, propylene or pentylene, and R$_3$ is imidazol-1-yl, imidazol-5-yl, 1-methylimidazol-2-yl, 4-methylimidazol-5-yl, 2- or 3-pyridyl, or imidazo[1,2-a]pyridin-3-yl, or (d) R$_1$ is hydroxy and R$_2$ is —A—R$_3$, wherein A is methylene, ethylene, propylene or pentylene, and R$_3$ is amino, dimethylamino, N-methyl-N-n-propylamino, N-methyl-N-n-pentylamino, N-cycloheptylamino, N-methyl-N-(2-phenylethyl)amino, N-methyl-N-(3-phenylpropyl)amino or N-methyl-N-(5-phenylpentyl)amino, N-methyl-N-(3-phenoxypropyl)amino, N-methyl-N-(2-phenylthioethyl)amino, N-methyl-N-(3-phenylthiopropyl)amino, N-methyl-N-[3-(2-pyridyl)propyl]amino, piperidin-1-yl, which is unsubstituted or substituted in 4-position by phenyl, or pyrrolidin-1-yl, which is unsubstituted or substituted in 3-position by 4-chlorophenyl, or is 1,5-dimethyl-3-azabicyclo[3.1.1]hept-3-yl, or is one of the methanebisphosphonic acid esters 5-benzoyl-3,4-dihydro-2H-pyrazole-3,3-diphosphonic acid tetraethyl ester and 1-(4-phenylthiobutylamino)methane-1,1-diphosphonic acid tetraethyl ester, or a pharmaceutically acceptable salt thereof, or any hydrate thereof.

5. A method according to claim 1, wherein the compound administered is selected from the following group:

4-amino-1-hydroxybutane-1,1-diphosphonic acid, 6-amino-1-hydroxyhexane-1,1-diphosphonic acid, 3-(N-methyl-N-n-pentylamino)-1-hydroxypropane-1,1-diphosphonic acid, 3-[N-(3-phenylpropyl)-N-methylamino]-1-hydroxypropane-1,1-diphosphonic acid, 3-(N-methyl-N-5-phenylpentylamino)-1-hydroxypropane-1,1-diphosphonic acid, 3-[N-methyl-N-3-(2-pyridyl)propylamino]-1-hydroxypropane-1,1-diphosphonic acid, 1-hydroxy-3-[N-methyl-N-(3-phenoxypropyl)amino]propane-1,1-diphosphonic acid, 1-hydroxy-3-[N-methyl-N-(2-phenoxyethyl)amino]propane-1,1-diphosphonic acid, 4-(4-phenylpiperidin-1-yl)-1-hydroxybutane-1,1-diphosphonic acid, 1-hydroxy-3-(1-piperidino)propane- 1,1-diphosphonic acid, 1-hydroxy-3-[3-(4-chlorophenyl)pyrrolidin-1-yl]propane-1,1-diphosphonic acid, 1-hydroxy-2-(imidazol-1-yl)ethane-1,1-diphosphonic acid, 2-(1-methylimnidazol-2-yl)ethane-1,1-diphosphonic acid, 1-hydroxy-2-(4-methylimidazol-5-yl)ethane-1,1-diphosphonic acid, 1-hydroxy-2-(imidazol-5-yl)

ethane-1,1-diphosphonic acid, 1-hydroxy-2-(3-pyridyl) ethane-1,1-diphosphonic acid, 2-(2-pyridyl)ethane-1,1-diphosphonic acid, 1-[(5-n-butyl-2-thiazolyl)anmino] methane-1,1-diphosphonic acid, 1-[(5-methyl-2-thiazolyl)amino]methane-1,1-diphosphonic acid, 1-[(2-thiazolyl)amino]-methane-1,1-diphosphonic acid, 1-(4-chlorophenylthio)methane-1,1-diphosphonic acid, 1,1-dichloromethane-1,1-diphosphonic acid, 3-(1,5-dimethyl-3-azabicyclo[3.1.1]hept-3-yl)-1-hydroxypropane-1,1-diphosphonic acid, 1-[(5-ethyl-2-thiazolyl)amino]methane-1,1-diphosphonic acid, 3-[N-(2-phenylethyl)-N-methyl-amino]-1-hydroxypropane-1,1-diphosphonic acid, 3-[N-(2-phenylthioethyl)-N-methylamino]-1-hydroxypropane-1,1-diphosphonic acid, 3-[N-(3-phenylthiopropyl)-N-methylamino]-1-hydroxypropane-1,1-diphosphonic acid, 1-hydroxy-3-(pyrrolidin-1-yl)propane-1,1-diphosphonic acid, 1-(N-cycloheptylamino)methane-1,1-diphosphonic acid, 2-(N,N-dimethylamino)-1-hydroxyethane-1,1-diphosphonic acid, 3-amino-1-hydroxypropane-1,1-diphosphonic acid, 3-(N,N-dimethylamino)-1-hydroxypropane-1,1-diphosphonic acid, 3-(N-methyl-N-n-propylamino)-1-hydroxypropane-1,1-diphosphonic acid, 1-[N-(4-phenylthiobutyl)-amino] methane-1,1-diphosphonic acid, 1-{N-[4-(2-pyridyl) thiobutyl]amino}nethane-1,1-diphosphonic acid, 1-(N-phenylaminothiocarbonyl)methane-1,1-diphosphonic acid, 5-benzoyl-3,4-dihydro-2H-pyrazole-3,3-diphosphonic acid tetraethyl ester, 1-(4-phenylthiobutylamino)methane-1,1-diphosphonic acid tetraethyl ester, 1-hydroxy-2-(imidazo[1,2-a]pyridin-3-yl)ethane-1,1-diphosphonic acid, and pharmaceutically acceptable salts thereof, and any hydrate thereof.

6. A method according to claim 1, wherein the compound administered is selected from the following group:

4-amino-1-hydroxybutane-1,1-diphosphonic acid, 6-amino-1-hydroxyhexane-1,1-dipthosphonic acid, 3-(N-methyl-N-n-pentylamino)-1-hydroxypropane-1, 1-diphosphonic acid, 1-hydroxy-2-(imidazol-1-yl) ethane-1,1-diphosphonic acid, 1-hydroxy-2-(3-pyridyl) ethane-1,1-diphosphonic acid, 1-(4-chlorophenylthio) methane-1,1-diphosphonic acid, 1,1-dichloromethane-1,1-diphosphonic acid, 3-[N-(2-phenylthioethyl)-N-methylamino]-1-hydroxypropane-1,1-diphosphonic acid, 1-hydroxy-3-(pyrrolidin-1-yl)-propane-1,1-diphosphonic acid, 1-(N-cycloheptylamino)methane-1, 1-diphosphonic acid, 3-amino-1-hydroxypropane-1,1-diphosphonic acid, 3-(N,N-dimethylamino)-1-hydroxypropane- 1,1-diphosphonic acid, 1-(N-phenylaminothiocarbonyl)methane-1,1-diphosphonic acid, 5-benzoyl-3,4-dihydro-2H-pyrazole-3,3-diphosphonic acid tetraethyl ester, 1-(4-phenylthiobutylamino)methane-1,1-diphosphonic acid tetraethyl ester, 1-hydroxy-2-(imidazo[1,2-a]pyridin-3-yl)ethane-1,1-diphosphonic acid, AJ-704 and BBR-2756, and pharmaceutically acceptable salts thereof, and any hydrate thereof.

7. A method according to claim 1, wherein the compound administered is a compound of formula Ia

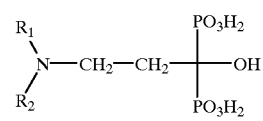

(Ia)

wherein $R_1$ and $R_2$ are each independently of the other hydrogen or $C_1$–$C_3$alkyl, or a pharmaceutically acceptable salt thereof, or any hydrate thereof.

8. A method according to claim 1, wherein the compound administered is 3-amino-1-hydroxypropane-1,1-diphosphonic acid, or a pharmaceutically acceptable salt thereof, or any hydrate thereof.

9. A method according to claim 1, wherein the compound administered is disodium pamidronate, or any hydrate thereof.

10. A method according to claim 1, wherein the compound administered is 1-hydroxy-2-(imidazol-1-yl)ethane-1,1-diphosphonic acid, or a pharmaceutically acceptable salt thereof, or any hydrate thereof.

11. A method according to claim 1, wherein the compound administered is 3-[N-(2-phenylthioethyl)-N-methylamino]-1-hydroxypropane-1,1-diphosphonic acid, or a pharmaceutically acceptable salt thereof, or any hydrate thereof.

12. A method of treating fractures in mammals according to claim 1, which comprises administering to a mammal in need thereof a dose of 0.15–4.90 mg/kg—in several partial doses or as a single dose—of 3-amino-1-hydroxypropane-1,1-diphosphonic acid, or a pharmaceutically acceptable salt thereof, or any hydrate thereof, within 7 days after fixation of the fracture, and optionally administering another dose of 0.15–4.90 mg/kg—in several partial doses or as a single dose—to the mammal within the next 30 days after administration of the first dose.

13. A method according to claim 12, wherein the compound administered is disodium pamidronate, or any hydrate thereof.

14. A method of treating fractures in mammals according to claim 1, which comprises administering to a mammal in need thereof a dose of 0.01–3.40 mg/kg—in several partial doses or as a single dose—of a methanebisphosphonic acid derivative selected from (a) 4-amino-1-hydroxybutane-1,1-diphosphonic acid, (b) 6-amino-1-hydroxyhexane-1,1-diphosphonic acid, (c) 3-(N-methyl-N-n-pentylamino)-1-hydroxypropane-1,1-diphosphonic acid, (d) 1-hydroxy-2-(imidazol-1-yl)ethane-1,1-diphosphonic acid, (e) 1-hydroxy-2-(3-pyridyl)ethane-1,1-diphosphonic acid, (f) 1-(4-chlorophenylthio)methane-1,1-diphosphonic acid, (g) 3-[N-(2-phenylthioethyl)-N-methylamino]-1-hydroxypropane-1,1-diphosphonic acid, (h) 1-hydroxy-3-(pyrrolidin-1-yl)propane-1,1-diphosphonic acid, (i) 3-(N,N-dimethylamino)-1-hydroxypropane-1,1-diphosphonic acid, (j) 1-(N-phenylaminothiocarbonyl)methane-1,1-diphosphonic acid, (k) 5-benzoyl-3,4-dihydro-2H-pyrazole-3,3-diphosphonic acid tetraethyl ester, (l) 1-(4-phenylthiobutylamino)methane-1,1-diphosphonic acid tetraethyl ester and (m) 1-hydroxy-2-(imidazo[1,2-a] pyridin-3-yl)ethane-1,1-diphosphonic acid, or a pharmaceutically acceptable salt thereof, or any hydrate thereof, within 7 days after fixation of the fracture, and optionally administering another dose of 0.01–3.40 mg/kg—in several partial doses or as a single dose—to the mammal within the next 30 days after administration of the first dose.

* * * * *

UNITED STATES PATENT AND TRADEMARK OFFICE
CERTIFICATE OF CORRECTION

PATENT NO. : 6,255,288 B1
DATED : July 3, 2001
INVENTOR(S) : Goodship et al.

It is certified that error appears in the above-identified patent and that said Letters Patent is hereby corrected as shown below:

<u>Title page,</u>
Item [74], should read:
-- Carol A. Loeschorn --.

<u>Column 14,</u>
Line 33, should read:
-- What is claimed is: --.

<u>Column 15,</u>
Line 65, should read:
-- $C_1$-$C_7$alkylene and $R_3$ is amino, di-$C_1$-$C_5$alkylamino, --.

<u>Column 16,</u>
Lines 61 and 65, respectively, should read:
-- 1-hydroxy-3-(1-piperidino)propane-1,1-diphosphonic --.
-- methylimidazol-2-yl)ethane-1,1-diphosphonic acid, --.

<u>Column 17,</u>
Line 28, should read:
-- thiobutyl]amino}methane-1,1-diphosphonic acid, 1-(N- --.
Lines 40 and 53, respectively, should read:
-- 6-amino-1-hydroxyhexane-1,1-diphosphonic acid, --.
-- hydroxypropane-1,1-diphosphinc acid, 1-(N- --.

Signed and Sealed this

Fifteenth Day of July, 2003

JAMES E. ROGAN
*Director of the United States Patent and Trademark Office*